US00PP17848P2

(12) United States Plant Patent
Klemm

(10) Patent No.: US PP17,848 P2
(45) Date of Patent: Jul. 3, 2007

(54) ***BRACTEANTHA* PLANT NAMED 'KLEBA04075'**

(50) Latin Name: *Bracteantha bracteata*
Varietal Denomination: KLEBA04075

(75) Inventor: Nils Klemm, Stuttgart (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 11/343,876

(22) Filed: Jan. 31, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Bracteantha* named 'KLEBA04075', characterized by its upright, compact and bushy growth habit; freely-flowering habit; bright yellow-colored involucral bracts and golden yellow-colored disc florets; and good garden performance.

1 Drawing Sheet

Botanical designation: *Bracteantha bracteata.*
Cultivar denomination: 'KLEBA04075'.

BACKGROUND OF THE INVENTION

The present invention relates to a new and distinct cultivar of *Bracteantha* plant, botanically known as *Bracteantha bracteata* and referred to by the name 'KLEBA04075'.

The new *Bracteantha* is a product of a planned breeding program conducted by the Inventor in Stuttgart, Germany. The objective of the program is to create and develop new compact and early-flowering *Bracteantha* cultivars with attractive involucral bract coloration and good garden performance.

The new *Bracteantha* originated from an open-pollination by the Inventor during the summer of 2001, of a proprietary selection of *Bracteantha bracteata* identified as code number SZ 005, not patented, as the female, or seed, parent with an unknown selection of *Bracteantha bracteata,* as the male, or pollen, parent. The new *Bracteantha* was discovered and selected by the Inventor as a plant within the progeny of the stated open-pollination in a controlled environment in Stuttgart, Germany in June, 2002.

Asexual reproduction of the new *Bracteantha* by terminal cuttings in a controlled environment in Stuttgart, Germany since 2002, has shown that the unique features of this new *Bracteantha* are stable and reproduced true to type in successive generations.

SUMMARY OF THE INVENTION

The new *Bracteantha* has not been observed under all possible environmental conditions. The phenotype may vary somewhat with variations in environment such as temperature and light intensity without, however, any variance in genotype.

The following characteristics have been repeatedly observed and are determined to be basic characteristics of 'KLEBA04075' and distinguish the new *Bracteantha* as a new and distinct cultivar:

1. Upright, compact and bushy growth habit.
2. Freely-flowering habit.

3. Bright yellow-colored involucral bracts and golden yellow-colored disc florets.
4. Good garden performance.

Plants of the new *Bracteantha* can be compared to plants of the female parent selection. Plants of the new *Bracteantha* are more compact than plants of the female parent selection.

Plants of the new *Bracteantha* can also be compared to plants of the cultivar Golden Beauty, not patented. Plants of the new *Bracteantha* differ from plants of the cultivar Golden Beauty primarily in plant shape as plants of the new *Bracteantha* are more upright than plants of the cultivar Golden Beauty. In addition, inflorescences of plants of the new *Bracteantha* have more involucral bracts and more disc florets than inflorescences of plants of the cultivar Golden Beauty.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Bracteantha.* The photograph comprises a side perspective view of a typical plant of 'KLEBA04075' grown in an outdoor nursery.

DETAILED BOTANICAL DESCRIPTION

The following observations and measurements describe plants grown in Stuttgart, Germany in a glass-covered greenhouse. During the production of the plants, day temperatures ranged from 16° C. to 22° C., night temperatures ranged from 12° C. to 16° C. and light levels ranged from 30 to 60 kilolux. Plants were grown in 12-cm containers and were pinched one time after planting. Plants had been growing for about three months when the photograph and description were taken. Color references are made to The Royal Horticultural Society Colour Chart, 1995 Edition, except where general terms of ordinary dictionary significance are used.

Botanical classification: *Bracteantha bracteata* cultivar KLEBA04075.

Parentage:

*Female or seed parent.*—Proprietary selection of *Bracteantha bracteata* identified as code number SZ 005, not patented.

*Male or pollen parent.*—Unknown selection of *Bracteantha bracteata.*

Propagation:

*Type.*—By cuttings.

*Time to initiate roots.*—Summer: About 16 days at 20° C. Winter: About 18 days at 20° C.

*Time to produce a rooted young plant.*—Summer: About three weeks at 20° C. Winter: About four weeks at 20° C.

*Root description.*—Fine to fibrous; white in color.

*Rooting habit.*—Freely-branching; dense.

Plant description:

*General appearance.*—Upright, compact and bushy growth habit; rounded plant form with inflorescences held above the foliage. Moderately vigorous growth habit. Freely branching habit, about eight to ten lateral branches per plant.

*Plant height.*—About 24 cm to 27 cm.

*Plant width.*—About 26 cm to 30 cm.

*Lateral branch (peduncle) description.*—Length: About 5 cm to 7 cm. Width: About 4 mm to 6 mm. Internode length: About 5 mm. Aspect: Mostly erect. Strong: Strong. Texture: Smooth, glabrous. Color: 143C.

*Foliage description.*—Arrangement: Alternate, single; sessile. Length: About 2 cm to 7 cm. Width: About 8 mm to 12 mm. Shape: Elliptic. Apex: Acute. Base: Obtuse. Margin: Entire. Texture, upper and lower surfaces: Rough, glabrous. Venation pattern: Pinnate. Color: Developing leaves, upper surface: 137C. Developing leaves, lower surface: 137D. Fully expanded leaves, upper surface: 137A; venation, 137C. Fully expanded leaves, lower surface: 137D; venation, 137D.

Flowering description:

*Inflorescence form.*—Daisy-type composite inflorescence form. Involucral bracts and disc florets develop arranged acropetally on a capitulum.

*Inflorescence longevity.*—Inflorescences last on the plant for about 8 to 18 days. Inflorescences persistent.

*Natural flowering season.*—Natural flowering season is during the summer in Germany; flowering continuous.

*Quantity of inflorescences.*—About 12 to 16 open inflorescences per plant.

*Fragrance.*—None detected.

*Inflorescence diameter.*—About 5 cm.

*Inflorescence depth (height).*—About 1.25 cm.

*Disc diameter.*—About 1.5 cm.

*Inflorescence buds.*—Length: About 1.5 cm to 2 cm. Diameter: About 1 cm. Shape: Roughly elliptic. Color: 8A.

*Involucral bracts.*—Quantity per inflorescence: About 50 in several whorls. Length: About 1.5 cm. Width: About 7 mm. Shape: Elliptic. Apex: Acute. Base: Attenuate. Margin: Entire. Texture, upper and lower surfaces: Smooth, glabrous; stiff. Color: When developing and fully developed, upper surface: 9A. When developing and fully developed, lower surface: 8A.

*Disc florets.*—Arrangement: Massed in the center of the receptacle with one whorl of filiform florets at the perimeter of the disc. Quantity per inflorescence: About 150. Shape: Tubular with five lobes. Length: about 7.5 mm. Diameter: About 1 mm. Color, immature and mature: Close to 23A.

*Androecium.*—Present only on disc florets; minute. Arrangement: Fused anther tube with five long thin linear anthers surrounding the style. Anther length: Less than 1 mm. Anther color: Yellow. Amount of pollen: Abundant. Pollen color: Yellow.

*Gynoecium.*—Present on both filiform and disc florets; minute. Quantity per floret: One. Style color: Close to 23A. Stigma shape: Bi-parted. Stigma color: Close to 23A.

*Seed.*—Seed development has not been observed.

Disease/pest resistance: Plants of the new *Bracteantha* have not been observed to be resistant to pathogens or pests common to *Bracteantha.*

Temperature tolerance: Plants of the new *Bracteantha* have been observed to tolerate temperatures from about 5° C. to about 35° C. and to have good garden performance.

It is claimed:

1. A new and distinct cultivar of *Bracteantha* named 'KLEBA04075', as illustrated and described.

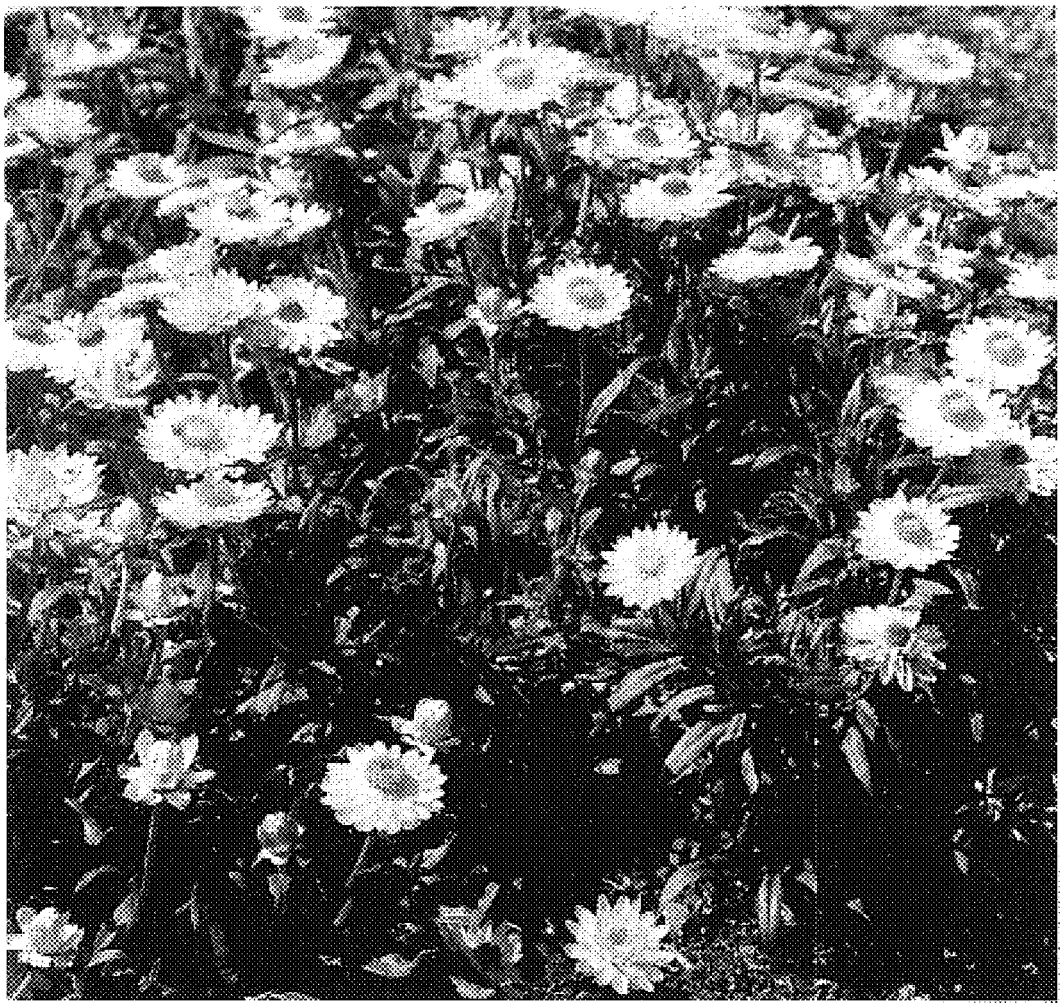

* * * * *